US00PP17827P2

(12) United States Plant Patent
Zaiger et al.

(10) Patent No.: US PP17,827 P2
(45) Date of Patent: Jun. 26, 2007

(54) INTERSPECIFIC TREE NAMED 'COT-N-CANDY'

(50) Latin Name: ***Prunus* species**
Varietal Denomination: Cot- N- Candy

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 27 days.

(21) Appl. No.: 11/314,466

(22) Filed: Dec. 22, 2005

(51) Int. Cl.
*A01H 5/00* (2006.01)

(52) U.S. Cl. ..... Plt./180

(58) Field of Classification Search ..... Plt./180
See application file for complete search history.

*Primary Examiner*—Kent Bell
*Assistant Examiner*—Annette H Para

(57) ABSTRACT

A new and distinct variety of interspecific tree. The following features of the tree and its fruit are characterized with the tree budded on 'Nemaguard' Rootstock (non-patented), grown on Hanford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Regular and productive bearer of medium size fruit.
2. Vigorous, semi-spreading tree growth.
3. Fruit having very good flavor and eating quality.
4. Fruit with white flesh.
5. Fruit with an attractive reddish pink blush.

1 Drawing Sheet

Botanical classification: Interspecific *Prunus* species.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of apricots, plums and interspecifics, which are known to us and mentioned herein, 'Tri-Gems' Apricot (U.S. Plant Pat. No. 6,755), 'Modesto' Apricot (U.S. Plant Pat. No. 2,543), 'Friar' Plum (non-patented) and 'Splash' Interspecific (U.S. Plant Pat. No. 14,583).

ORIGIN OF THE VARIETY

The new and distinct variety of interspecific tree, [*Prunus armeniaca*×((*Prunus salicina*×(*Prunus salicina*×*Prunus armeniaca*)×(*Prunus salicina*×*Prunus armeniaca*)×*Prunus armeniaca*] was originated by us in our experimental orchard located near Modesto, Calif. as an open pollinated seedling selection from our proprietary interspecific seedling with the field identification number '9Z37-A'. The proprietary parent (9Z37-A) originated from the crosses of the following parents 'Tri-Gems' Apricot (U.S. Plant Pat. No. 6,755), 'Modesto' Apricot (U.S. Plant Pat. No. 2,543), 'Friar' Plum (non-patented), 'Splash' Interspecific (U.S. Plant Pat. No. 14,583), a proprietary plumcot with the field identification number '4G1180' and a white apricot of unknown parentage. A large number of these open pollinated seedlings were budded on older trees of 'Nemaguard' Rootstock (non-patented), to induce earlier fruit production, one budded seedling exhibited desirable fruit and tree growth characteristics and was selected in 1998 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

A new and distinct variety of interspecific tree [Apricot×((Plum×Plumcot)×Plumcot)×Apricot] is of large size, vigorous, semi spreading growth and a productive and regular bearer of medium size, white flesh fruit with excellent eating quality. The fruit is further characterized by a slight reddish pink blush, firm flesh and being relatively uniform in size throughout the tree. In comparison to its immediate parent (9Z37-A), the fruit of the new variety has firmer flesh, higher soluble solids (Brix) and is approximately 3 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large. Usually pruned to 3 to 3.5 meters in height and width for economical harvesting of fruit. Average spread 3 to 3.5 meters, varies with different cultural practices.

*Vigor.*—Vigorous, growing 1.5 to 2 meters in height the first growing season, varies with fertility of soil, climatic conditions and cultural practices.

*Form.*—Semi-spreading, usually pruned to vase shape.

*Branching habit.*—Semi-spreading, crotch angle approximately 40°, increases with heavy crop load.

*Productivity.*—Productive, thinning and spacing of fruit necessary. Fruit set varies slightly with climatic conditions at bloom time.

*Bearer.*—Regular, has set an adequate crop 4 consecutive years with no alternate bearing observed.

*Fertility.*—Self-fertile.

*Density.*—Medium dense. Pruned to vase shape to allow air and sunlight to center of tree to enhance fruit color and health of fruit spurs.

*Hardiness.*—Hardy in all stone fruit growing areas in California. Tree grown in USDA Hardiness Zone 9. Winter chilling requirement approximately 800 hours at or below 45° F.

Trunk:

*Size.*—Medium stocky. Average circumference 43.2 cm at 28 cm above ground on a 6 year old tree.

*Stocky.*—Medium stocky.

*Texture.*—Medium shaggy, increases with age of tree.

*Color.*—Varies from 10YR 5/2 to 10YR 4/2.

Branches:

*Size.*—Medium. Average circumference 14.9 cm at 1.2 meters above ground. Crotch angle approximately 40°, increases with heavy crop load.

*Surface texture.*—New growth relatively smooth. Mature growth medium rough, roughness increases with age.

*Lenticels.*—Average number 16 in a 25.8 sq cm surface. Size — average length 2.7 mm. Average width 1.6 mm. Color varies from 7.5YR 7/6 to 10YR 7/8.

*Color.*—New growth varies from 2.5GY 5/8 to 5R 3/6, varies with exposure to sunlight. Old growth varies from 2.5YR 2/4 to 7.5YR 6/2, varies with age of growth.

Leaves:

*Size.*—Medium. Average length 81.4 mm. Average width 68.9 mm.

*Form.*—Ovate.

*Apex.*—Acuminate.

*Base.*—Obtuse.

*Margin.*—Doubly serrate.

*Thickness.*—Medium.

*Surface texture.*—Upper surface relatively smooth with slight indentations over midrib and pinnate venation, glabrous. Lower surface relatively smooth with slight ridging from midvein and pinnate venation, glabrous.

*Petiole.*—Average length 29.2 mm. Average width 1.5 mm. Very shallow, longitudinal groove. Surface glabrous. Color varies from 5GY 6/6 to 5R 3/8, varies with amount of exposure to direct sunlight.

*Glands.*—Globose. Small. Average length 0.8 mm. Average diameter 0.6 mm. Number varies from 1 to 6, average 4. Located on upper portion of the petiole and lower portion of the leaf blade. Color varies from 5GY 5/6 to 5R 3/6.

*Color.*—Upper surface varies from 5GY 3/6 to 5GY 3/4. Lower surface varies from 5GY 4/4 to 5GY 4/6. Midvein color varies from 5GY 8/6 to 5GY 7/4.

Flower buds:

*Size.*—Small to medium. Average length 12.8 mm. Average diameter 7.3 mm.

*Hardiness.*—Hardy with respect to California winters.

*Form.*—Conical, becoming elongated before opening.

*Pedicel.*—Average length 1.5 mm. Average width 1.9 mm. Color varies from 10Y 7/6 to 10Y 7/8.

*Color.*—Varies from 7.5RP 6/10 to 7.5RP 5/12.

*Number of buds per spur.*—Average number 3, varies from 1 to 6.

Flowers:

*Size.*—Medium. Average height 13.1 mm. Average diameter 26.8 mm.

*Petals.*—Number 5, alternately arranged to sepals. Orbicular, narrows at point of attachment. Average length 12.2 mm. Average width 12.0 mm. Margin — sinuate. Color varies from 5RP 8/4 to 5RP 6/10, fades with age of flower.

*Sepals.*—Number 5, alternately arranged to petals. Shape — triangular, apex rounded. Margin entire. Both surfaces glabrous. Average length 4.8 mm. Average width 3.9 mm. Color — upper surface varies from 5R 3/10 to 10Y 7/4. Lower surface varies from 5R 3/8 to 7.5R 2/8.

*Stamens.*—Average number per flower 30. Average filament length 10.0 mm. Filament color varies from 7.5RP 9/2 to N 9.5/ (white). Anther color varies from 5Y 9/6 to 5Y 8/8.

*Pollen.*—Abundant, self fertile. Color varies from 2.5Y 7/10 to 2.5Y 7/12.

*Pistil.*—Normally 1. Surface pubescent. Average length 14.7 mm. Position of stigma average of 1.6 mm above anthers. Color varies from 7.5Y 8.5/4 to 7.5Y 8/6.

*Fragrance.*—Moderate aroma.

*Blooming period.*—Date of First Bloom Feb. 16, 2005. Date of Petal Fall Feb. 24, 2005, varies slightly with climatic conditions.

*Color.*—Varies from 5RP 8/4 to 5RP 6/10, fades as flowers age.

*Number flowers per flower bud.*—Usually 1, varies from 1 to 2.

*Pedicel.*—Average length 2.0 mm. Average width 2.0 mm. Color varies from 10Y 7/8 to 2.5GY 7/6.

Fruit:

*Maturity when described.*—Firm ripe.

*Date of first picking.*—Jun. 12, 2005.

*Date of last picking.*—Jun. 18, 2005, varies slightly with climatic conditions.

*Size.*—Medium. Average diameter axially 50.0 mm. Average transversely in suture plane 49.6 mm. Average weight 62.5 grams, varies slightly with fertility of the soil, amount of thinning and climatic conditions.

*Form.*—Globose, slightly flattened toward suture plane.

*Suture.*—Shallow, extends from base to apex.

*Ventral surface.*—Slightly lipped.

*Apex.*—Varies from rounded to slightly retuse.

*Base.*—Flat to slightly retuse.

*Cavity.*—Rounded to slightly elongated in suture plane. Average depth 2.7 mm. Average diameter 7.2 mm.

Stem:

*Size.*—Small. Average length 6.7 mm. Average diameter 3.5 mm.

*Color.*—Varies from 2.5GY 5/8 to 5GY 5/6.

Flesh:

*Ripens.*—Evenly.

*Texture.*—Firm, smooth apricot texture.

*Fibers.*—Few, small, tender.

*Firmness.*—Firm.

*Aroma.*—Moderate.

*Amydgalin.*—Undetected.

*Eating quality.*—Excellent.

*Flavor.*—Excellent, good balance between acid and sugar.

*Juice.*—Moderate, enhances flavor.

*Brix.*—Average 15.3°, varies slightly with amount of fruit per tree and climatic conditions.

*Color.*—Varies from 2.5Y 9/2 to 5Y 9/2. Pit cavity varies from 2.5Y 8.5/2 to 2.5Y 8/4.

Skin:

*Thickness.*—Medium.

*Surface.*—Smooth.

*Down.*—Moderate, pubescence short in length.

*Tendency to crack.*—None.

*Color.*—Ground color varies from 5Y 9/6 to 5Y 8/7. Light blush where exposed to sun, color varies from 7.5YR 7/10 to 5R 4/10.

*Tenacity.*—Tenacious to flesh.

*Astringency.*—None.

Stone:

*Type.*—Freestone.

*Size.*—Medium. Average length 26.0 mm. Average width 21.7 mm. Average thickness 13.3 mm.

*Form.*—Ovoid.

*Base.*—Usually flat, varies from flat to slightly rounded.

*Apex.*—Rounded, no sharp point.

*Surface.*—Slightly pitted throughout. One shallow groove on each side of the suture creating a small, narrow ridge.

*Sides.*—Unequal, one side extending further from suture plane.

*Ridges.*—Very small, narrow ridge next to groove on each side of suture.

*Tendency to split.*—None.

*Color.*—Varies from 2.5Y 7/4 to 2.5Y 3/4 when dry.

Kernal:

*Form.*—Ovate.

*Taste.*—Bitter.

*Viability.*—Viable, complete embryo development.

*Size.*—Average length 17.4 mm. Average width 12.3 mm. Average depth 8.1 mm.

*Skin.*—Color varies from 2.5Y 9/2 to 5Y 8.5/2 when dry.

Use: Dessert. Market — local and long distance.

Keeping quality: Good, held firm in storage 2 weeks at 38° to 42° F. without shriveling, internal breakdown of flesh or appreciable loss of eating quality.

Shipping quality: Good, showed minimal skin scarring or bruising of flesh in picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct interspecific tree, substantially as illustrated and described, characterized by its large size, vigorous, semi-spreading growth and being a regular and productive bearer of medium size, white flesh fruit that has an attractive reddish pink blush; the fruit is further characterized by being relatively uniform in size throughout the tree, having excellent flavor and eating quality with a good balance between acid and sugar.

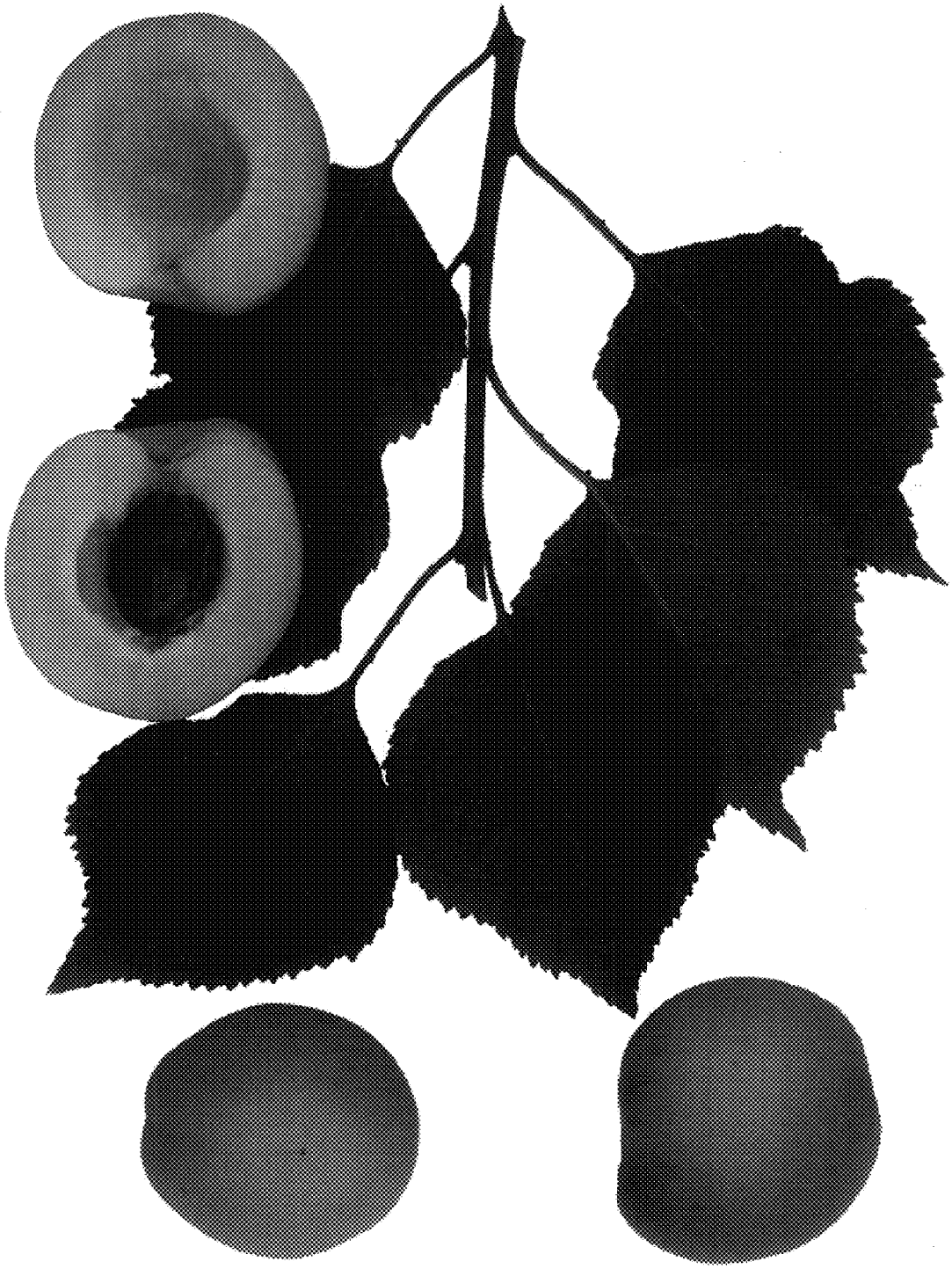

* * * * *